(12) United States Patent
Pesce

(10) Patent No.: US 6,730,819 B1
(45) Date of Patent: May 4, 2004

(54) ARTICLES COMPRISING OXIDIZING AND HEMOLYTIC AGENTS

(75) Inventor: Antonella Pesce, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/914,490

(22) PCT Filed: Mar. 2, 2000

(86) PCT No.: PCT/US00/05501

§ 371 (c)(1),
(2), (4) Date: Aug. 29, 2001

(87) PCT Pub. No.: WO00/51655

PCT Pub. Date: Sep. 8, 2000

(30) Foreign Application Priority Data

Mar. 5, 1999 (EP) .............................................. 99103930

(51) Int. Cl.[7] ............................ A61F 13/15; A61F 13/20
(52) U.S. Cl. ........................................ 604/360; 604/359
(58) Field of Search .................................. 604/359, 360

(56) References Cited

U.S. PATENT DOCUMENTS

| 2,542,909 | A | 2/1951 | DeWet |
| 3,490,454 | A | 1/1970 | Goldfarb et al. |
| 4,363,322 | A | 12/1982 | Anderson |
| 4,847,089 | A | 7/1989 | Kramer et al. |

FOREIGN PATENT DOCUMENTS

| EP | 0 510 619 A1 | 10/1992 |
| EP | 0 604 919 A1 | 7/1994 |
| WO | WO 92/11238 A2 | 7/1992 |
| WO | WO 92/16681 A2 | 10/1992 |
| WO | WO 95/22655 A1 | 8/1995 |
| WO | WO 98/26808 | 6/1998 |

*Primary Examiner*—Glenn K. Dawson
*Assistant Examiner*—Michele Kidwell
(74) *Attorney, Agent, or Firm*—Kevin C. Johnson

(57) ABSTRACT

The present invention relates to articles coming into contact with bodily fluids, preferably absorbent articles like sanitary napkins and pantiliners, which comprise an oxidising agent having a reduction potential higher than that of the reaction of $Fe^{2+}$ to $Fe^{3+}$ togather with a hemolytic agent. In a preferred embodiment the articles further comprise an additional odour control agent.

16 Claims, No Drawings

ARTICLES COMPRISING OXIDIZING AND HEMOLYTIC AGENTS

FIELD OF THE INVENTION

This invention relates to articles, such as absorbent articles comprising an oxidising agent as described herein together with a hemolytic agent.

BACKGROUND OF THE INVENTION

Articles like absorbent articles for example are designed to be worn by humans to absorb bodily fluids, such as menstrual fluid. Examples of absorbent articles include sanitary napkins, pantiliners, tampons, interlabial devices, and the like.

In use, these absorbent articles are known to acquire a variety of malodours compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odours. These compounds may be present in the bodily fluid or may be developed by chemical reactions and/or any fluid degradation mechanisms once the bodily fluid is absorbed into the absorbent article like for example a feminine pad. In addition bodily fluids usually contain microorganisms and/or enzymes that can also generate malodorous by products as a result of degradation mechanisms like putrefactive degradation, acid degradation, proteins degradation, fat degradation and the like. Unpleasant odours which emanate from absorbent pads when in use may make the wearer feel self conscious.

Another drawback associated with such absorbent articles is that the bodily fluid like menstruation which comes into contact with the absorbent articles may make the wearer feel unclean.

It is an object of the present invention to provide an absorbent article that delivers a better feeling and more acceptable cleanness level for the person wearing it when it comes into con t act with bodily fluids like menstruation/blood. More particularly, it is an object of the present invention to provide both outstanding cleanness level and outstanding odour control over a wide range of malodorous compounds.

It has now been found that the above needs can be addressed by combining an oxidising agent having a reduction potential higher than the reduction potential of the reaction Fe2+ to Fe3+, preferably a peroxyacid like ε-phtalimido peroxyhexanoic acid (PAP), or a diacyl peroxide like dibenzoyl peroxide, benzoyl lauroyl peroxide and/or dilauroyl peroxide, together with a hemolytic agent, preferably a zwitterionic surfactant like a quaternary ammonium surfactant, in an article coming into contact with bodily fluid like menstruation, preferably a disposable absorbent article.

Indeed, the present invention due to the presence of the oxidizing agent as described herein and the hemolytic agent provides an absorbent article capable of changing the color of the menstruation (red blood color) to a pale red color and even to a whitish color. Without to be bounded by theory, it is speculated that the blood bleaching is due to the oxidation by means of the oxidizing agent as defined herein, of the hemoglobin $Fe^{2+}$ to $Fe^{3+}$ with formation of methemoglobin (brown color) followed by protein denaturation resulting in a whitening of the brown color. The hemolytic agent has been found to enhance the iron oxidation by facilitating the access of the oxidizing agent to the hemoglobin. Indeed, the hemolytic agent is able to disrupt the erythrocyte membrane, thereby facilitating the oxidation reaction of the hemoglobin iron by the oxidizing agent.

In other words, the presence of the hemolytic agent allows instantaneous oxidizing of the menstruation as soon as it comes into contact with both the hemolytic agent and the oxidizing agent present in an absorbent article as well as the desired bleaching effect with reduced level of oxidizing agent, as compared to the use of the same absorbent article containing only the oxidizing agent without the hemolytic agent.

It has further been surprisingly discovered that the combination of a oxidising agent having a reduction potential higher than of the reaction $Fe^{2+}$ to $Fe^{3+}$, preferably a peroxyacid like ε-phtalimido peroxyhexanoic acid (PAP), or a diacyl peroxide like dibenzoyl peroxide, benzoyl lauroyl peroxide and/or dilauroyl peroxide, together with an hemolytic agent, preferably a zwitterionic surfactant like a quaternary ammonium surfactant, in an article, like an absorbent article coming into contact with bodily fluids, results in significantly improved odour control as compared to the odour control obtained with the same article comprising only the oxidising agent without the hemolytic agent. Indeed, this combination gives effective odour control over a broader malodorous range.

In a preferred embodiment of the present invention the peroxyacids and diacyl peroxides as described herein are used as the oxidising agent. These oxidising agents are particularly preferred herein as they deliver the outstanding benefits described herein (blood bleaching and odour control) without the generation of malodorous smelling by products like chlorine derivatives and ammonium derivatives, when they come into contact with bodily fluids. Also these oxidising agents do not interfere with the decoloration obtained according to the present invention as their own color is white. Finally these oxidising agents have an excellent safety profile.

Whereas the present invention is preferably directed to absorbent articles like pantiliners, feminine napkins, tampons, interlabial pads and the like, other articles may include the two essential agents described herein too for the purpose of effective blood bleaching and effective odour control when in contact with blood containing bodily fluids. Indeed, other applications include other articles designed to be worn in contact with the body such as clothing, bandages, thermal pads, acne pads, cold pads, compresses, surgical pads/dressings and the like, body cleansing articles like impregnated wipes (e.g. baby wipes, wipes for feminine intimate hygiene), impregnated tissues, towels and the like.

BACKGROUND ART OF THE INVENTION

U.S. Pat. No. 4,363,322 discloses deodorising and disinfecting liquid-absorbing products such as a sanitary napkin, a compress or a diaper, comprising a liquid absorbing material and inside the product at a distance from its outer edges a substance which gives off oxygen in contact with moisture like peroxides, ozonides, superoxides, oxo-ozonides and the like.

EP-A-268 459 discloses a body fluid absorbing article provided with one absorbent member comprising 50% to 99% by weight of a fibrous material and 50% to 1% by weight of an absorbent polymer, which absorbent member contains at least one compound selected from sulphur-containing reducing agents, antioxidants and oxidising agents.

Other odour control agents are known in the art. Examples of these types of compounds include activated carbons, clays, zeolites, silicates, starches, cyclodextrine, ion exchange resins and various mixture thereof as for example described in EP-A-348 978, EP-A-510 619, WO 91/12029, WO 91/11977, WO89/02698, and/or WO 91/12030.

None of these references disclose absorbent articles with an oxidising agent as defined herein in combination with a hemolytic agent for improving the wearing comfort of such articles by both controlling the odour emanating from the bodily fluid like menstruation and diminishing the red color of the menstruation to pale red or even whitish color. This color change allows to decrease and even eliminate the fear and embarrassment that accompanies bleeding.

SUMMARY OF THE INVENTION

The present invention relates to an article, preferably a disposable absorbent article, comprising at least one oxidising agent having a reduction potential higher than that of the reaction of $Fe^{2+}$ to $Fe^{3+}$, and at least one hemolytic agent. In a preferred embodiment of the invention the article also comprises an additional odour control agent, preferably at least an absorbing gelling material.

The present invention also encompasses the use, as an odour control system, of an oxidising agent having a reduction potential higher than that of the reaction of $Fe^{2+}$ to $Fe^{3+}$, preferably a peroxyacid and/or a diacyl peroxide, together with a hemolytic agent, preferably a zwitterionic surfactant.

The present invention further encompasses the use, of an oxidising agent having a reduction potential higher than that of the reaction of $Fe^{2+}$ to $Fe^{3+}$, preferably a peroxyacid and/or a diacyl peroxide, together with a hemolytic agent, preferably a zwitterionic surfactant, in an article, typically a disposable absorbent article, in order to provide improved cleanness when said article comes into contact with blood-containing bodily fluids.

DETAILED DESCRIPTION OF THE INVENTION

The articles, for decoloring the red color associated with blood containing bodily fluids and for controlling odour associated with bodily fluids, according to the present invention comprise as an essential element an oxidising agent having a reduction potential higher than that of the reaction of $Fe^{2+}$ to $Fe^{3+}$, and a hemolytic agent.

By "article" it is meant herein any tridimentional solid material being able to receive/carry the oxidising agent and hemolytic agent as described herein after. Preferred articles according to the present invention are disposable absorbent articles that are designed to be worn in contact with the body of a user and to receive fluids discharged from the body, such as disposable absorbent pantiliners, sanitary napkins, catamenials, tampons, interlabial pads/inserts and the like. Other suitable articles according to the present invention include other articles designed to be worn in contact with the body such as clothing, bandages, thermal pads, acne pads, cold pads, compresses, surgical pads/dressings and the like, as well as body cleansing articles like impregnated wipes (e.g. baby wipes, wipes for feminine intimate hygiene), impregnated tissues, towels, and the like.

By "bodily fluids" it is meant herein blood-containing fluids produced by human or animal body occurring naturally (e.g., menstruation) or accidentally like for instance in the case of skin cutting.

The Oxidising Agent

The oxidising agent according to the present invention are any oxidising agent known to those skilled in the art that have a reduction potential higher than the one of the reaction of $Fe^{2+}$ to $Fe^{3+}$.

The standard reduction potential $E°$ value at 25° C. and at a pressure of 1 atm for $Fe^{3+}+e^-\rightleftharpoons Fe^{2+}$ is 0.771V. Thus the oxidising agents for use herein have a standard reduction potential $E°$ of more than 0.771V. Standard reduction potential is a criteria well known in the chemical field for defining the oxidation/reduction power of a given material. It is for example illustrated in CRC handbook of Chemistry and Physics, $76^{th}$ edition, David R. Lide, Ph.D. CRC Press, page 8-21 to 8-33.

A suitable way to measure the standard potential is done by reference to SHE (Standard Hydrogen Electrode) by mean of an electrochemical cell. This method is for instance illustrated in KIRK OTHMER, Encyclopedia of chemical technology, 1981, Vol. 15, page 39–40.

Unlike the tables which list standard potentials, values for oxidising agents are experimental values dependent from the experimental conditions, electrodes and techniques used. Accordingly the reduction potential may be reported as experimental values, usually a half-wave potential (E1/2 in polarography) or a peak potential (Ep in cyclic voltammetry). Whatever the conditions/electrodes/techniques used, the oxidising agents suitable for use herein have a reduction potential higher than the reduction potential of the reaction $Fe^{2+}$ to $Fe^{3+}$. In other words, for defining the oxidising agents herein the reaction $Fe^{2+}$ to $Fe^{3+}$ is taken as a reference in the same test conditions.

The oxidising agents for use herein include oxygen bleaches like peroxygen bleaches or mixtures thereof.

Such peroxygen bleaches include hydrogen peroxide, percarbonates, persulphates, perborates, peroxyacids, alkyl hydroperoxides, peroxides, diacyl peroxides, ozonides, supereoxides, oxo-ozonides, periodates, salts thereof or mixtures thereof. Peroxyacids and diacyl peroxides are preferred herein.

Suitable hydroperoxides for use herein include tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide.

Suitable peroxides for use herein include for example lithium peroxide, sodium peroxide, potassium peroxide, ammonium peroxide, calcium peroxide, rubidium peroxide, cesium peroxide, stromtium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, nickel peroxide, other alkali metal salts thereof or alkaline earth metal salts thereof or mixture thereof.

Suitable superoxides for use herein include for example lithium superoxide, sodium superoxide, potassium superoxide, calcium superoxide, rubidium superoxide, cesium superoxide, stromtium superoxide, barium superoxide, other alkali metal salts thereof or alkaline earth metal salts thereof or mixture thereof.

Suitable ozonides for use herein include for example lithium ozonide, sodium ozonide, potassium ozonide, rubidium ozonide, cesium ozonide, ammonium ozonide, tetramethyl ammonium ozonide, stromtium ozonide, barium ozonide, magnesium ozonide, other alkali metal salts thereof or alkaline earth metal salts thereof or mixture thereof.

Suitable perborates for use herein include for example sodium perborate, potassium perborate, ammonium perborate or other alkali metal salts thereof or alkaline earth metal salts thereof or mixture thereof.

Suitable persulphates for use herein include sodium persulphate, potassiumdipersulphate, potassium persulphate as well as other alkali metal salts thereof or mixture thereof.

Other suitable peroxygen bleaches also include diacetylperoxydicarbonate, 1,1bis(terbutylperoxy)-3,3,5-trimetylcyclohexane, di(1-naphtyl) peroxide, tert-butyl perbenzoate, O,O-t-buthyl-O-isopropyl mono-peroxycarbonate, percarbonates like stearyl percarbonate, 2-ethylhexyl percarbonate and sec-butyl percarbonate and corresponding perborates and persulphates.

Suitable diacyl peroxides for use herein are according to the formula:

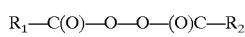

$$R_1—C(O)—O—O—(O)C—R_2$$

wherein $R_1$ and $R_2$ can be the same or different and are selected from the group of substituted or unsubstituted, saturated or unsaturated, linear, branched or cyclic hydrocarbon groups having from 1 to 50 carbon atoms, preferably from 2 to 40 and more preferably from 4 to 30 carbon atoms.

Suitable diacyl peroxides for use herein include those wherein $R_1$ and $R_2$ are independently an aliphatic group, those wherein $R_1$ and $R_2$ are independently an aromatic ring and those wherein $R_1$ is an aliphatic group and $R_2$ is an aromatic ring.

Typically $R_1$ and $R_2$ are independently an aliphatic group having from 2 to 40, more preferably 4 to 30, even more preferably 5 to 20 carbon atoms. These aliphatic groups may be linear, branched, cyclic, saturated, unsaturated, substituted, unsubstituted or mixtures thereof. Preferably the aliphatic groups are linear and comprise from 4 to 20 carbon atoms, and more preferably 8 to 18 carbon atoms. Where such an aliphatic group is substituted, the carbon atom is preferably substituted with a halide or sulfate-containing or nitrogen-containing functionality such as SO3-, SO4-, NO2, NR3+ where R=H or an alkyl chain containing from 1 to 5 carbon atoms.

Typically $R_1$ and $R_2$ may be independently a mono or polycyclic aromatic ring, a homo or heteroaromatic ring, substituted or unsubstituted having from 2 to 50 carbon atoms and mixtures thereof. Where such an aromatic ring is substituted, the carbon atom is preferably substituted with a halide, sulphur-containing group, nitrogen-containing group or an alkyl chain wherein the number of carbon atoms ranges from 1 to 20, most preferably from 4 to 10. Suitable sulphur-containing or nitrogen-containing substituents include SO3-, SO4-, NO2, NR3+ where R=H or an alkyl chain containing from 1 to 5 carbon atoms. Preferred aromatic ring is benzene.

Particularly suitable diacyl peroxides for use herein are those wherein $R_1$ is an aliphatic group as defined herein before and $R_2$ is a mono or polycyclic aromatic ring, a homo or heteroaromatic ring, substituted or unsubstituted as defined herein before. Such preferred diacyl peroxides are benzoyl alkanoyl peroxides wherein the alkanoyl group has from 4 to 20 carbon atoms and more preferably from 8 to 18 carbon atoms.

Suitable diacyl peroxides for use herein are dilauroyl peroxide, didecanoyl peroxide, dimyristoyl peroxide, dibenzoyl peroxide, di-4-methylbenzoyl peroxide, di-p-methoxybenzoyl peroxide, acetyl benzoyl peroxide, benzoyl stearoyl peroxide, benzoyl decanoyl peroxide, benzoyl cetyl peroxide, para-alkyl benzoyl lauroyl peroxide, para-alkyl benzoyl decanoyl peroxide, para-alkyl benzoyl cetoyl peroxide, di-4-phenylbenzoyl peroxide, di-t-butylperoxide, t-butyl cumyl peroxide, diethyl peroxide, diacetyl peroxide, dicumyl peroxide, diheptanoyl peroxide, didecanoyl peroxide, benzoyl lauroyl peroxide, diheptanoyl peroxide, distearoyl peroxide, disuccinyl peroxide, 3,5,5-trimethylhexanoyl peroxide, or mixtures thereof.

Highly preferred diacyl peroxides herein are dilauroyl peroxide which may be commercially available as flakes from AKZO NOBEL under the name Laurox®, or as powder under the name Laurox S®, or in suspension in water under the name Laurox W 40®, or dibenzoyl peroxide which may be commercially available from AKZO NOBEL under the name Lucidol® in powder form or Lucidol W40® in the form of a suspension in water, and/or benzoyl lauroyl peroxide.

The aromatic alkanoyl peroxides described herein like benzoyl lauroyl peroxide are easily synthesized by persons skilled in the art, see for example Organic Peroxides Vol. 1; page 65, edited by Daniel Swern of Wiley Interscience.

Suitable peroxyacids for use herein are according to the following formula:

$$R_3—CO3H$$

wherein $R_3$ is a substituted or unsubstituted, saturated or unsaturated, linear or branched hydrocarbon group having from 1 to 25 carbon atoms or a cyclic group having from 3 to 32 carbon atoms and optionally at least one heteroatom or a cyclic alkyl group having from 4 to 32 carbon atoms and optionally at least one heteroatom.

Typically $R_3$ is a substituted or unsubstituted, linear or branched alkyl group or alkenyl group having from 1 to 25 carbon atoms, more preferably from 1 to 14 carbon atoms, even more preferably from 3 to 10, and most preferably from 4 to 6. $R_3$ may also typically be an aryl group having from 3 to 32 carbon atoms, preferably from 3 to 25, more preferably from 6 to 20, even more preferably from 8 to 15 carbons atoms, or an aryl alkyl group having from 4 to 32 total carbon atoms, preferably from 4 to 25, more preferably from 6 to 20 and even more preferably from 8 to 13, or an heterocyclic group containing from 3 to 32 carbon atoms, preferably from 3 to 25, more preferably from 3 to 20 carbon atoms, even more preferably from 5 to 15 and from 1 to 5 hetero atoms, preferably 1 to 3, wherein the hetero atoms are independently selected from the group consisting of oxygen, nitrogen and sulfur, and preferably is nitrogen or oxygen, or an heterocyclic alkyl group containing from 4 to 32 total carbon atoms, preferably from 4 to 25, more preferably from 4 to 22, even more preferably from 6 to 18 and from 1 to 5 hetero atoms, preferably 1 to 3, wherein the hetero atoms are independently selected from the group consisting of oxygen, nitrogen and sulfur, and preferably is nitrogen or oxygen.

The preferred peroxyacids according to the present invention are those wherein $R_3$ is a cyclic group or cyclic alkyl group, preferably a heterocyclic group or heterocyclic alkyl group.

Even more preferred herein are the peroxyacids according to the following formulae:

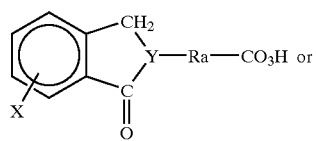

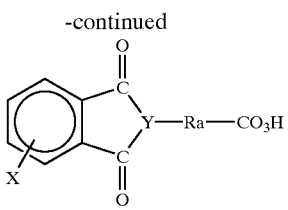

wherein Ra is a substituted or unsubstituted, saturated or unsaturated, linear or branched hydrocarbon group having from 1 to 14 carbon atoms, Y is an heteroatom and X are substituents in position ortho or meta independently selected from the group of hydrogen, hydroxy, halogen, carboxy, aliphatic saturated or unsaturated, linear or branched, hydrocarbon group having from 1 to 10 carbon atoms, or a mixture thereof.

Preferably Ra is a substituted or unsubstituted, linear or branched alkyl group or alkenyl group having from 2 to 12 carbon atoms, preferably from 2 to 10, more preferably from 2 to 8, even more preferably from 3 to 6 and most preferably 5 carbon atoms. Preferably Y is an heteroatom selected from the group consisting of oxygen, nitrogen and sulfur, and more preferably is nitrogen atom (>N—). Preferably X are substituents on position ortho or meta independently selected from the group consisting of hydrogen, hydroxy, aliphatic linear or branched alkyl group or alkenyl group having from 1 to 10 carbon atoms, preferably from 2 to 7 and most preferably from 3 to 5 carbon atoms. Highly preferred herein all the substituents X are independently hydrogen.

The preferred peroxyacids for use according to the present invention are pthalimido- and phtalamido peroxyalkanoic acids.

Highly preferred peroxyacids herein is ε-pthalimido peroxyhexanoic acid which may be commercially available from AUSIMONT under the name PAP®, or EURECO® (in granule form), Eureco WKC® (in wet granule form) or Eureco HC® (in powdered active form).

Other suitable oxidising agents for use herein include inorganic oxides like urea peroxide, potassium permanganate, potassium chromate, potassium dichromate, ruthenium tetra-oxide, osmium tetra-oxide, cerium compounds including cerium oxides, cerium hydroxides, cerium hydrated oxides, cerium oxysalts and the like, lead compounds including lead oxides, lead tetraoxides, lead acetates, lead tetracetates and the like, manganese compounds including manganese permanganate, manganese oxide and the like, ozone, hydrazine and derivatives thereof and the like.

These oxidising agents are able to oxidise the hemoglobin $Fe^{2+}$ to $Fe^{3+}$ with the formation of methemoglobin followed by the denaturation of protein, this results in decoloration of the blood red color to a more whitish color. Indeed the blood color is due to erythrocytes containing hemoglobin, a macromolecule comprising four peptide chains (heteropolymers) and four hemecomplexes. An hemecomplex consists of an organic ligand with an iron atom $Fe^{2+}$ coordinated to it through four nitrogen atoms. The hemecomplexes give the hemoglobin and thus the erythrocytes containing it, their red color.

The oxidising agents herein effectively control the odour associated with bodily fluids. Indeed, they prevent the formation of odour by for example blocking enzymatic and/or microbial activity and they combat the malodorous compounds already present by oxidising them into non-smelling compounds.

Indeed, it is speculated that the oxidising agents herein (preferably the peroxyacids as described herein and/or diacyl peroxides as described herein) oxidise sensitive sulphidryl and sulphur bonds typically present in enzymes, thereby deactivating the enzymes which otherwise would have contributed to the normal metabolism of the micro-organisms. It is further speculated that these oxidising agents oxidise double bonds in lipophilic metabolites like for instance nutriments (e.g., unsaturated fat) for the micro-organisms, thereby rendering these nutriments inefficient for the microbial growth which otherwise would have resulted in generation of malodorous compounds. It is further believed that the oxidising agents described herein disrupt the chemiosmotic function of the lipoprotein cytoplasmatic membrane of the microbe/bacteria cells and thus disrupt the transport function at the cell walls. This later disruption is especially noticeable with the hydrophobic oxidising agents like the cyclic or cyclic alkyl peroxyacids, namely the ones according to the chemical formulae described herein as well as the diacyl peroxides described herein. By 'hydrophobic oxidising agents' it is meant herein those oxidising agents that can be solubilised in the lipidic layers of the cell wall of the micro-organisms. Highly preferred hydrophobic oxidising agents for use herein are the phtalimido- and phtalamido peroxyalkanoic acids, and the diacyl peroxides according to the formula defined herein before especially the benzoyl alkanoyl peroxides, dialkanoyl peroxides and diaromatic peroxides like dibenzoyl peroxide. Indeed, it is speculated that the hydrophobic groups of these oxidising agents facilitate and enhance the reaction of the oxidising agents with the lipoproteins of the cell wall of the micro-organisms.

In a preferred embodiment of the present invention the oxidising agents herein are the peroxyacids (e.g., phtalimido peroxyalkanoic acid and/or phtalamido peroxyalkanoic acid) and/or diacyl peroxides (e.g., the benzoyl alkanoyl peroxides, dialkanoyl peroxides and diaromatic peroxides like dibenzoyl peroxide). Indeed in contrast to the use of some inorganic peroxides like persulfate, the peroxyacids and diacyl peroxides as described herein are free of deactivation by catalase and/or peroxidase enzymes that are present in bodily fluids.

An additional advantage of the preferred oxidising agents herein like the peroxyacids and diacyl peroxides as described herein is that the generation of malodorous smelling by products like chlorine derivatives and ammonium derivatives is avoided, when they come into contact with bodily fluids.

Typically, the articles according to the present invention like disposable absorbent articles comprise the oxidizing agent or a mixture thereof at a level of from 1 $gm^{-2}$ to 250 $gm^{-2}$, preferably from 5 to 150 $gm^{-2}$, more preferably from 10 $gm^{-2}$ to 100 $gm^{-2}$ and most preferably from 20 $gm^{-2}$ to 70 $gm^{-2}$

The Hemolytic Agent

The articles of the present invention comprise as an essential compound a hemolytic agent or a mixture thereof.

By 'hemolytic agent' it is meant herein any compound able to disrupt/leak the membrane of erythrocytes. This membrane is a selectively permeable barrier between the erythrocyte intracellular environment and the extracellular environment. This membrane is made of phosphatidilcoline, sphingomyelin, phosphatidilserine, phosphatidilethanolamine and proteins like spectrine.

The hemolytic agent herein boosts the blood bleaching of the oxidizing agent. It is speculated that the presence of the hemolytic agent herein allows faster and almost complete disruption of the erythrocyte cell, thus providing instantaneous oxidation of the hemoglobin iron by the oxidizing agent. In other words, the erythrocyte membrane disruption allows an increased amount of contact between the hemoglobin iron and the oxidizing agent resulting in significantly enhanced blood bleaching. Hence, this further contributes to use less oxidizing agent within the absorbent article to obtain the desired blood bleaching as compared to the use of the oxidizing agent alone without the hemolytic agent.

The hemolytic agents herein also further improve the odour control performance of the oxidising agents. It is speculated that different mechanisms may be involved depending on the hemolytic agents used. For instance the hemolytic agents as described herein, especially the anionic surfactants, the nonionic surfactants, the amphoteric surfactants and/or the zwitterionic surfactants like for instance the quaternary ammonium surfactants, act as a carrier for the oxidising agents as described herein, especially for the peroxyacids and diacyl peroxides herein (which can be classified as hydrophobic oxidising agents) and thus contribute to bring the oxidising agents into closer contact not only with the hemoglobin iron but also with the oxidable malodorous compounds contained in the bodily fluid (including not only the hydrophobic oxidable malodorous compounds but also more hydrophilic ones). Also the hemolytic agents for use herein, especially the zwitterionic surfactants like for instance the quaternary ammonium surfactants are suitable to disrupt/leak the cell walls of microorganisms. In other words, they also act as antimicrobial agents and, thus further contribute to control the odour associated with microbial activity occurring in the bodily fluids like menstruation. Indeed it is speculated that the hemolytic agents herein disrupt the chemiosmotic function of the lipoproteine cytoplasmatic membrane of microbe/bacteria cells and thus disrupt the transport function at the cell walls.

Suitable hemolytic agents for use herein include any hemolytic surfactant known to those skilled in the art including nonionic surfactants, anionic surfactants, amphoteric surfactants and/or zwitterionic surfactants.

Other suitable hemolytic agents for use herein include biguanide and derivatives thereof, organic sulfur compounds, organic nitrogen compounds, phenyl and phenoxy compounds, phenolic compounds, aldehydes like glutaraldehyde, formaldehyde, glyoxal, parabens like ethyl paraben, propyl paraben, methyl paraben, organic acids and carboxylic acids, alcohols in particular aliphatic alcohols having from 1 to 16 carbon atoms, preferably from 1 to 6 (e.g., methanol, ethanol, propanol, isopropanol, butanol, pentanol, octanol) and aromatic alcohols having from 6 to 30 total carbon atoms (e.g., naphtol) and mixtures thereof.

Suitable phenolic compounds for use herein include o-penyl-phenol, o-benzyl(p-chlorophenol), 4-tertamylphenol and mixtures thereof.

Highly preferred hemolytic agents for use herein are the zwitterionic surfactants and mixtures thereof.

Nonionic Surfactants

Particularly suitable for use herein as hemolytic nonionic surfactants are hydrophobic nonionic surfactants having an HLB (hydrophilic-lipophilic balance) below 16, preferably below 15, more preferably below 12, and most preferably below 10. Furthermore the preferred hemolytic nonionic surfactant are linear ones. The hydrophobic linear nonionic surfactants have been found to provide good hemolytic properties.

Suitable hydrophobic nonionic surfactants to be used herein are fatty alcohol alkoxylates (e.g., ethoxylates and/or propoxylates) which are commercially available with a variety of fatty alcohol chain lengths and a variety of alkoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Accordingly, preferred alkoxylated alcohols for use herein are nonionic surfactants having an HLB below 16 and according to the formula RO(E)e(P)pH where R is a hydrocarbon chain of from 2 to 30 carbon atoms, e is ethylene oxide and p is propylene oxide, and e and p which represent the average degree of, respectively ethoxylation and propoxylation, are of from 0 to 15. The hydrophobic moiety of the nonionic compound can be a primary or secondary, straight or branched alcohol having from 8 to 30 carbon atoms. Preferred nonionic surfactants for use in the compositions according to the invention are the condensation products of ethylene oxide with alcohols having a straight linear alkyl chain, having from 6 to 30 carbon atoms, wherein the degree of ethoxylation is from 1 to 10, preferably from 1 to 5. Such suitable nonionic surfactants are commercially available from Shell, for instance, under the trade name Dobanol® or Neodol®, or from BASF under the trade name Lutensol®.

Other suitable hemolytic nonionic surfactants include the polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octane, and nonane.

Anionic Surfactants

Suitable anionic surfactants for use herein are as following:

Suitable alkyl sulphonates for use herein include water-soluble salts or acids of the formula $RSO_3M$ wherein R is a $C_6$–$C_{20}$ linear or branched, saturated or unsaturated alkyl group, preferably a $C_{12}$–$C_{18}$ alkyl group and more preferably a $C_{14}$–$C_{16}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

Suitable alkyl aryl sulphonates for use herein include water-soluble salts or acids of the formula $RSO_3M$ wherein R is an aryl, preferably a benzyl, substituted by a $C_6$–$C_{20}$ linear or branched saturated or unsaturated alkyl group, preferably a $C_{12}$–$C_{18}$ alkyl group and more preferably a $C_{14}$–$C_{16}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

An example of a C14–C16 alkyl sulphonate is Hostapur® SAS available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright&Wilson.

Suitable alkyl sulphate surfactants for use herein are according to the formula $R_1SO_4M$ wherein $R_1$ represents a hydrocarbon group selected from the group consisting of straight or branched alkyl radicals containing from 6 to 20 carbon atoms and alkyl phenyl radicals containing from 6 to 15 carbon atoms in the alkyl group. M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

Suitable alkyl alkoxylated sulphate surfactants for use herein are according to the formula $RO(A)_mSO_3M$ wherein R is an unsubstituted $C_6$–$C_{20}$ alkyl or hydroxyalkyl group having a $C_6$–$C_{20}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines such as ethylamine, diethylamine, triethylamine, mixtures thereof, and the like. Exemplary surfactants are $C_{12}$–$C_{18}$ alkyl polyethoxylate (1.0) sulfate, $C_{12}$–$C_{18}E(1.0)M$, $C_{12}$–$C_{18}$ alkyl polyethoxylate (2.25) sulfate, $C_{12}$–$C_{18}E(2.25)M$, $C_{12}$–$C_{18}$ alkyl polyethoxylate (3.0) sulfate $C_{12}$–$C_{18}E(3.0)$, and $C_{12}$–$C_{18}$ alkyl polyethoxylate (4.0) sulfate $C_{12}$–$C_{18}E(4.0)M$, wherein M is conveniently selected from sodium and potassium.

Suitable $C_6$–$C_{20}$ alkyl alkoxylated linear or branched diphenyl oxide disulphonate surfactants for use herein are according to the following formula:

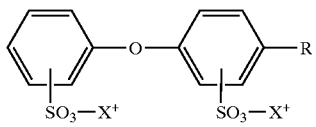

wherein R is a $C_6$–$C_{20}$ linear or branched, saturated or unsaturated alkyl group, preferably a $C_{12}$–$C_{18}$ alkyl group and more preferably a $C_{14}$–$C_{16}$ alkyl group, and X+ is H or a cation, e.g., an alkali metal cation (e.g., sodium, potassium, lithium, calcium, magnesium and the like). Particularly suitable $C_6$–$C_{20}$ alkyl alkoxylated linear or branched diphenyl oxide disulphonate surfactants to be used herein are the C12 branched di phenyl oxide disulphonic acid and C16 linear di phenyl oxide disulphonate sodium salt respectively commercially available by DOW under the trade name Dowfax 2A1® and Dowfax 8390®.

Other anionic surfactants useful herein include salts (including, for example, sodium, potassium, ammonium, and substituted ammonium salts such as mono-, di- and triethanolamine salts) of soap, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), alkyl polyethoxy carboxylates such as those of the formula $RO(CH_2CH_2O)_kCH_2COO$—$M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Preferred anionic surfactants for use herein are the alkyl sulphate surfactants and/or the alkyl alkoxylated sulphate surfactants as described herein before. Particularly suitable for use herein is for instance dodecyl sodium ethoxylate sulphate commercially available from Conoco under the name Alfonic 1412-5®.

Amphoteric Surfactants

Suitable amphoteric surfactants for use herein include amine oxides having the following formula $R_1R_2R_3NO$ wherein each of $R_1$, $R_2$ and $R_3$ is independently a saturated substituted or unsubstituted, linear or branched hydrocarbon chains of from 1 to 30 carbon atoms. Preferred amine oxide surfactants to be used according to the present invention are amine oxides having the following formula $R_1R_2R_3NO$ wherein $R_1$ is an hydrocarbon chain comprising from 1 to 30 carbon atoms, preferably from 6 to 20, more preferably from 8 to 16, most preferably from 8 to 12, and wherein $R_2$ and $R_3$ are independently substituted or unsubstituted, linear or branched hydrocarbon chains comprising from 1 to 4 carbon atoms, preferably from 1 to 3 carbon atoms, and more preferably are methyl groups. $R_1$ may be a saturated substituted or unsubstituted linear or branched hydrocarbon chain.

Suitable amine oxides for use herein are for instance natural blend C8–C10 amine oxides as well as C12–C16 amine oxides commercially available from Hoechst.

Zwitterionic Surfactants

Suitable zwitterionic surfactants for use herein contain both cationic and anionic hydrophilic groups on the same molecule at a relatively wide range of pH's. The typical cationic group is a quatemary ammonium group, although other positively charged groups like phosphonium, imidazolium and sulfonium groups can be used. The typical anionic hydrophilic groups are carboxylates and sulfonates, although other groups like sulfates, phosphonates, and the like can be used.

A generic formula for some zwitterionic surfactants to be used herein is $$R_1-N^+(R_2)(R_3)R_4X^-$$

wherein $R_1$ is a hydrophobic group; $R_2$ is hydrogen, $C_1$–$C_6$ alkyl, hydroxy alkyl or other substituted C1–C6 alkyl group; $R_3$ is hydrogen, $C_1$–$C_6$ alkyl, hydroxy alkyl or other substituted $C_1$–$C_6$ alkyl group which can also be joined to $R_2$ to form ring structures with the N, or a $C_1$–$C_6$ carboxylic acid group or a $C_1$–$C_6$ sulfonate group; $R_4$ is a moiety joining the cationic nitrogen atom to the hydrophilic group and is typically an alkylene, hydroxy alkylene, or polyalkoxy group containing from 1 to 10 carbon atoms or hydrogen; and X is the hydrophilic group (as called counteranion) which is a carboxylate group, a sulphate group, a sulfonate group, an halogen or hydroxide.

Preferred hydrophobic groups $R_1$ are aliphatic or aromatic, saturated or unsaturated, substituted or unsubstituted hydrocarbon chains that can contain liking groups such as aryl groups, amido groups or ester groups. More preferred $R_1$ is a linear or branched alkyl group containing from 1 to 30 carbon atoms, preferably from 1 to 24, more preferably from 10 to 20 and most preferably from 8 to 18. In general, the simple alkyl groups are preferred for cost and stability reasons.

Preferred zwitterionic surfactants for use herein include betaine surfactants, sulphobetaine surfactants, and quaternary ammonium surfactants, derivatives thereof or mixtures thereof. Said betaine, sulphobetaine surfactants and/or quaternary ammonium surfactants are preferred herein as they further contribute to the antimicrobial activity of the oxidising agent herein. For instance they have been found to be particularly suitable to increase the permeability of the bacterial cell wall, thus allowing the oxidising agent to enter the cell. In other words, they further contribute to the outstanding odour control provided by the articles according to the present invention.

Suitable betaine and sulphobetaine surfactants for use herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference.

Preferred betaine and sulphobetaine surfactants herein are according to the formula

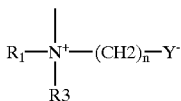

wherein $R_1$ is a hydrocarbon chain containing from 1 to 24 carbon atoms, preferably from 8 to 18, more preferably from 12 to 14, wherein R2 and R3 are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of $R_1$, $R_2$ and $R_3$ hydrocarbon chains is from 14 to 24 carbon atoms, or mixtures thereof.

Examples of particularly suitable betaine surfactants include C12–C18 alkyl dimethyl betaine such as coconut-betaine and C10–C16 alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Highly preferred zwitterionic surfactants for use herein are quaternary ammonium surfactants according to the formula $R_1R_2R_3R_4N^+X^-$, wherein X is a counteranion such as halogen, methyl sulphate, methyl sulphonate, or hydroxide, $R_1$ is a saturated or unsaturated, substituted or unsubstituted, linear or branched alkyl group containing from 1 to 30 carbon atoms, preferably from 8 to 20, more preferably from 12 to 20 and $R_2$, $R_3$ and $R_4$ are independently hydrogen, or saturated or unsaturated, substituted or unsubstituted, linear or branched alkyl groups containing from 1 to 4 carbon atoms, preferably from 1 to 3 and more preferably methyl. In highly preferred quaternary ammonium surfactants herein $R_1$ is a $C_{10}$–$C_{18}$ hydrocarbon chain, most preferably $C_{12}$, $C_{14}$, or $C_{16}$, and $R_2$, $R_3$ and $R_4$ are all three methyl, and X is halogen, preferably bromide or chloride, most preferably bromide.

Other particularly suitable quaternary ammonium compounds for use herein are quaternary ammonium compounds containing alkyl amide and carboxylic acid groups, ether groups, as well as cyclic quaternary ammonium compounds, which can be chlorides, dichlorides, bromides, methylsulphates, chlorophenates, cylcohexylsulphamates or salts of other acids. Among the possible cyclic quatemary ammonium compounds are the following:

alkylpyridinium chlorides and/or sulphates, the alkyl group being preferably cetyl, dodecyl or hexadecyl group;

alkylisoquinolyl chlorides and/or bromides, the alkyl group being preferably dodecyl group.

Examples of quaternary ammonium surfactants are myristyl trimethylammonium methyl sulphate, cetyl trimethylammonium methyl sulphate, lauryl trimethyl ammonium bromide, stearyl trimethyl ammonium bromide (STAB), cetyl trimethyl ammonium bromide (CTAB) and myristyl trimethyl ammonium bromide (MTAB). Such trimethyl quatemary ammonium surfactants may be commercially available from Hoechst, or from Albright & Wilson under the trade name Empigen CM®. Further examples of quaternary ammonium surfactants include alkyl dimethyl benzyl ammonium chloride, benzyl ammonium chloride, octyl decyl dimethyl ammonium chloride, dioctyl dimethyl ammonium chloride, didecyl dimethyl ammonium chloride, alkyl dimethyl ammonium saccharinate, cetylpyridinium and mixtures thereof.

Highly preferred quatemary ammonium surfactants for use herein are cetyl trimethyl ammonium salts, lauryl trimethyl ammonium salts commercially available from for example Hoechst and/or benzyl ammonium salts like benzyl ammonium chloride commercially available from Fluka.

Other specific zwitterionic surfactants have the generic formulas:

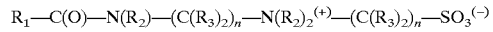

or

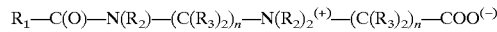

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen.), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$-$C_{14}$ fatty acylamidopropylene (hydroxypropylene)sulfobetaine that is available from the Sherex Company under the trade name "Varion CAS sulfobetaine"®.

Typically, the articles according to the present invention like disposable absorbent articles comprise the hemolytic agent or a mixture thereof at a level of from 0.5 $gm^{-2}$ to 100 $gm^{-2}$, preferably from 2.5 to 75 $gm^{-2}$, more preferably from 5 $gm^{-2}$ to 50 $gm^{-2}$ and most preferably from 10 $gm^{-2}$ to 30 $gm^{-2}$.

Optional Agents

The articles according to the present invention preferably further comprise other conventional agents or mixtures thereof.

For instance additional odour control agents or combinations thereof, known in the art for this purpose may be used herein. These agents can typically be classified according to the type of odour the agent is intended to combat. Odors may be chemically classified as being acidic, basic or neutral.

Alternatively, the odor control agents may be categorised with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carbonates (e.g., sodium carbonate), bicarbonates (e.g., sodium bicarbonate), phosphates (e.g., sodium phosphate), sulphates (e.g., zinc and copper sulphates), carboxylic acids such as citric acid, lauric acid, boric acid, adipic acid and maleic acid, activated carbons, clays, zeolites, silicas, absorbent gelling materials (AGM) and starches. Such odor control agents and systems are disclosed in more details hereinafter and for example in EP-A-348 978, EP-A-510 619, WO 91/12029, WO 91/11977, WO 91/12030, WO 81/01643 and WO 96/06589.

Suitable odour control agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odor control agent for use herein is a buffer system, such as citric acid and sodium bicarbonate, sodium phosphate and sorbic acid buffer systems. Also, buffer systems having a pH of from 7 to 10 as described for example in WO94/25077 may be useful herein.

Alternative odor control agents are ion exchange resins such as those described in U.S. Pat. No. 4,289,513 and U.S. Pat. No. 3,340,875.

Masking agents such as perfumes may also be used as odor control agents herein.

Typically, the articles according to the present invention like disposable absorbent articles may comprise the additional odour control agent or a mixture thereof at a level of from 1 $gm^{-2}$ to 400 $gm^{-2}$, preferably from 10 to 300 $gm^{-2}$, more preferably from 20 $gm^{-2}$ to 200 $gm^{-2}$ and most preferably from 50 $gm^{-2}$ to 100 $gm^{-2}$.

Absorbent Gelling Odor Control Materials

As is well-known from recent commercial practice, absorbent gelling materials (sometimes referred to as "supersorbers") are becoming broadly used in absorbent articles. AGM's are materials which have fluid-absorbing properties.

Such materials are highly preferred herein as the optional odor control agent due to their dual function of absorbing fluids and odors.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractables content in synthetic urine of no more than about 17%, preferably no more than about 10% by weight of the absorbent gelling material.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 micron s are less desirable. Particles having a smallest dimension larger than about 2 mm may also cause a feeling of grittyness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

The amount of absorbent gelling material particles used in absorbent article will typically range from 10 gm$^{-2}$ to 150 gm$^{-2}$, preferably from 30 gm$^{-2}$ to 110 gm$^{-2}$, more preferably from 55 gm$^{-2}$ to 85 gm$^{-2}$.

Silica Odor Control Agent

Particularly suitable herein as an additional odor control agent is silica. Silica, i.e. silicon dioxide $SiO_2$ exists in a variety of crystalline forms and amorphous modifications, any of which are suitable for use herein. In particular, silicas having a high surface area or in agglomerated form are preferred. Silica molecular sieves are not considered to be within the definition of silica as used herein. Preferably the silica is in a highly purified form such that is contains at least 90%, preferably 95%, more preferably 99% silicon dioxide. Most preferably the silica is silica gel having a 100% silica content. Alternatively, the silica may be provided from other sources such as metal silicates including sodium silicate.

Zeolite Odor Control Agent

The use and manufacture of zeolite material is well know in the literature and is described in the following reference texts: ZEOLITE SYNTHESIS, ACS Symposium Series 398, Eds. M. L. Occelli and H. E Robson (1989) pages 2–7; ZEOLITE MOLECULAR SIEVES, Structure, Chemistry and Use, by D. W. Breck, John Wiley and Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University of Microfilms International, Ann Arbor, Mich., pages 2–8.

Zeolites are crystalline aluminosilicates of group IA and group IIA elements such as Na, K, Mn, Ca and are chemically represented by the empirical formula:

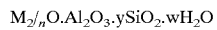

$$M_{2/n}O.Al_2O_3.ySiO_2.wH_2O$$

where y is 2 or greater, n is the cation valence, and w is the water content in the voids of the zeolite.

Structurally, zeolites are complex, crystalline inorganic polymers based on an infinitely extending framework of $AlO_4$ and $SiO_4$ tetrahedra linked to each other by sharing of oxygen ions. This framework structure contains channels or interconnected voids that are occupied by the cations and water molecules.

The structural formula of a zeolite is based on the crystal unit cell, the smallest unit of structure, represented by

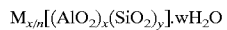

$$M_{x/n}[(AlO_2)_x(SiO_2)_y].wH_2O$$

where n is the valence of cation M, w is the number of water molecules per unit cell, x and y are the total number of tedrahedra per unit cell, y/x usually having values of 1–5.

Zeolites may be naturally derived or synthetically manufactured. The synthetic zeolites being preferred for use herein. Suitable zeolites for use herein include zeolite A, zeolite P, zeolite Y, zeolite X, zeolite DAY, zeolite ZSM-5, or mixtures thereof. Most preferred is zeolite A.

According to the present invention the zeolite is preferably hydrophobic. This is typically achieved by increasing the molar ratio of the $SiO_2$ to $AlO_2$ content such that the ratio of x to y is at least 1, preferably from 1 to 500, most preferably from 1 to 6.

The Absorbent Article

The oxidizing agent, the hemolytic agent and optional additional odour control agent may be incorporated into the absorbent article by any of the methods disclosed in the art, for example layered on the core of the absorbent article or mixed within the fibres of the absorbent core.

These materials are preferably incorporated between two layers of cellulose tissue. Optionally these materials may be bonded between two cellulose tissue layers with, for example, a hot melt adhesive or any suitable bonding system, as described in WO 94/01069.

In one embodiment of the present invention the oxidizing agent and hemolytic agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers ($120\ gm^{-2}$) that would be incorporated as an optional component in the present invention. The intermediate layer comprises in particular a polyethylene powder as thermoplastic material which is mixed with the oxidizing agent, the hemolytic agent and optional additional odour control agent. The mixture is then heated such that the polyethylene melts and glues the laminate layers together. Adhesive lines are preferably also placed on the edges of the laminate to ensure that the edges of the laminate stick and any loose oxidising agent as described herein and hemolytic agent present do not fall out of the laminate.

Alternatively, the polyethylene powder may be replaced by a conventional glue for instance those commercially available from ATO Findley under the name H20-31® to glue the laminate layers and/or components together. Advantageously this method step allows to avoid the heating step necessary when using polyethylene powder.

In a preferred embodiement the oxidizing agent and hemolytic agent on one side and the optional additional odour control agent if present on the other side are incorporated between two layers of cellulose tissues separated by another layer of cellulose in order to avoid possible reaction between the oxidizing agent and the additional odour control agent.

The oxidizing agent, the hemolytic agent and the optional additional odour control agent may be distributed independently homogeneously or non homogeneously over the entire absorbent article or in at least one layer of the topsheet or in at least one layer of the core or any mixture thereof. The oxidizing agent, the hemolytic agent and the optional additional odour control agent may be distributed independently homogeneously or non homogeneously on the whole surface of the desired layer or layers, or on one or several area of the surface layer/layers to which it is positioned (e.g. central area and/or surrounding area like the edges of a layer of the absorbent article) or mixtures thereof. Preferably the oxidizing agent and the hemolytic agent are located towards the topsheet or is located in the topsheet itself (preferably the secondary topsheet).

In a preferred embodiment the oxidizing agent and hemolytic agent are positioned such that at least a portion of the fluid discharge comes into contact with said oxidizing agent before the additional odour control agent (e.g., AGM/silica/zeolite) if present. In particular, the oxidizing agent is located in a separate layer from the additional odour control agent. Preferably the oxidizing agent is located towards the topsheet or is located in the topsheet itself (preferably the secondary topsheet) and the additional odour control agent if present, is located further away from the topsheet than the oxidizing agent. In one embodiment of the present invention, the oxidizing agent is positioned in at least one of the topsheet layers and the additional odour control agent if present is positioned in the core. More preferably, the oxidizing agent is located at the fluid discharge entry point of the absorbent article.

The oxidizing agent, the hemolytic agent and the optional additional odour control agent may be incorporated independently as a powder or a granulate within the absorbent article or can be sprayed in the form of for example an oxidising agent-containing solution within the absorbent article. When used in a granulate or particulate form the oxidizing agent and the hemolytic agent may be granulated separately and then mixed together or granulated together.

Typical disposable absorbent articles according to the preferred embodiments of the present invention are those as described herein after:

The Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials in combination with suitable carriers.

Suitable carriers include materials which are conventionally utilized in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orion), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer which provides the user facing surface of the topsheet and a second layer between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non woven fabrics and films.

In a preferred embodiment of the present invention at least one of the layers, preferably the upper layer, of the topsheet comprises a hydrophobic, liquid permeable apertured polymeric film. Preferably, the upper layer is provided by a film material having apertures which are provided to facilitate liquid transport from the wearer facing surface towards the absorbent structure. If present the lower layer preferably comprises a non woven layer, an apertured formed film or an airlaid tissue.

The term apertured polymeric topsheet as used herein refers to topsheets comprising at least one layer or a multiplicity of layers wherein at least one layer is formed from a continuous or uninterrupted film material wherein apertures are created. It has been surprisingly discovered that apertured polymeric film topsheets yield significantly better odour control than other types of topsheets such as for example thermal bonded nonwoven materials.

In general the apertured polymeric topsheet of the present invention is compliant, soft feeling, and non-irritating to the wearer's skin. Further, the topsheet is fluid pervious permitting fluids (e.g., menses and/or urine) to readily penetrate through its thickness. Suitable apertured polymeric film topsheets for use herein include polymeric apertured formed films, thermoplastic films, apertured plastic films, and hydroformed thermoplastic films; porous foams; net-like reticulated foams and thermoplastic films; and thermoplastic scrims.

Preferred topsheets for use in the present invention are selected from apertured formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

Suitable topsheets in the field of three dimensional formed film are described in EP 0 018 020 and EP 0 059 506. Especially preferred in a three dimensional formed polymeric topsheet having openings in the shape of regular pentagons which are regularly spaced and have an opening of 0.41 square millimeter. The openings are spaced 0.37 square millimeters apart transversely and 0.25 millimeters longitudinally. This topsheet has an initial opening (preforming) thickness of about 25 m a final (post forming) thickness of about 0.53 mm and an open area of from 25% to about 40%.

Another formed film topsheet which is especially preferred is one having openings of two shapes; regular pentagons having an area of about 0.21 square millimeters and an irregular hexagon having an area of 1.78 square millimeters. The openings are distributed so that the distance between the sides of the figures is about 0.37 mm to about 0.42 mm. The preforming and post forming film thickness are respectively 0.25 and 0.43 mm. This film has an open area of about 33.7%. Both films are made according to the teachings of the above mentioned patents.

A third form suitable topsheet comprises two separate perforated polymeric films superimposed one on the other.

The body surface of the formed film topsheet of the present invention may also be hydrophilic so as to help liquid to transfer through the topsheet faster than if the body surface was not hydrophilic. In this manner the likelihood that menstrual fluid will flow off the topsheet rather than flowing into and being absorbed by the absorbent structure is diminished. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred sideflaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more clothlike appearance. Further, the backsheet can permit vapors to escape from the absorbent structure, i.e. be breathable, while still preventing extrudates from passing through the backsheet. Also breathable backsheets comprising several layers, e.g. film plus non-woven structures, can be used.

Odor Control Test

The odor reduction is measured by for example an in vitro sniff test. This test consists in analyzing the products (e.g., pads) (including references) by expert graders that express their judgment about (un)pleasantness of the odor of the product.

Blood Decoloration Test

The blood decoloration may be measured visually by expert graders. Alternatively the blood decoloration may also be measured by spectrophotometer (from X-Rite LTd). By means of this instrument it is possible for instance to measure the level of lightness, redness and/or yellowness of the pads once the instrument calibration has been completed versus a reference.

The present invention is further illustrated by the following examples.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper which covers the external adhesive layer. The side of the absorbent fibrous core was then exposed by slightly shifting the water impermeable plastic bottom layer and subsequently, the fibrous core was split into two halves, each having approximately the same thickness, along a plane which is parallel to the plane of the napkin itself. The oxidising agent and the hemolytic agent were homogeneously distributed between these two fibrous layers which were then joined together to reconstitute the absorbent core.

The water impermeable inner backsheet was then put back into its original position and the wrap around perforated coverstock was sealed along the cut by means of e.g. a double sided adhesive tape.

Samples were produced using the method above, containing the odor control systems as described hereinbelow.

The oxidising agent (0.8 g) used was $\epsilon$-phtalimido peroxyhexanoic acid commercially available from Ausimont or dibenzoyl peroxide commercially available from AKZO NOBEL under the name Lucidol® or benzoyl lauroyl peroxide. The hemolytic agent (0.2 g) used was cetylpyridinium chloride commercially available from SIGMA

Example B

In example B samples were produced using the same method as in Example A, except that the hemolytic agent (0.2 g) used was benzyl ammonium chloride commercially available from Fluka instead of cetylpyridinium chloride.

Example C

In example C samples were produced using the same method as in Example A, except that AGM was added on top of the oxidising agent and hemolytic agent. The AGM (0.8 g) used is commercially available from Dow Chemicals (XZ 9589001).

Example D

In example D samples were produced using the same method as in Example C, except that the hemolytic agent (0.2 g) used was benzyl ammonium chloride commercially available from Fluka instead of cetylpyridinium chloride.

Example E

Other pads were prepared by following the method of example A except that after having split the fibrous core into two halves, the oxidising agent and the hemolytic agent were homogeneously distributed onto the upper halve fibrous layer (i.e. the fibrous layer halve intended to be closer to the topsheet) and that AGM was homogeneously distributed onto the lower halve fibrous layer (i.e., the one intended to be closer to the backsheet of the pad once reconstituted). Then a layer of airlaid tissue (19 mm*70 mm of low basis weight) available from Fripa under the code/name NCB Tissue HWS was positioned between the two halve fibrous layers which are then joined together to reconstitute the absorbent core. The presence of the airlaid tissue between the two fibrous layer avoids direct contact between the oxidising agent and the AGM.

These samples were produced using as oxidising agent (0.8 g) of ε-phtalimido peroxyhexanoic acid commercially available from Ausimont or dibenzoyl peroxide commercially available from AKZO NOBEL under the name Lucidol® or benzoyl lauroyl peroxide. The AGM (0.8 g) used is commercially available from Dow Chemicals (XZ 9589001). The hemolytic agent (0.2 g) used was cetylpyridinium chloride commercially available from SIGMA.

Example F

In example F samples were produced using the same method as in Example E, except that the hemolytic agent (0.2 g) used was benzyl ammonium chloride commercially available from Fluka instead of cetylpyridinium chloride.

All the above pads showed outstanding cleanness level and outstanding odour control over a wide range of malodorous compounds.

What is claimed is:

1. An absorbent article comprising at least an oxidizing agent having a reduction potential higher than the reduction potential of the reaction $Fe^{2+}$ to $Fe^{3+}$ together with a hemolytic agent, wherein said oxidizing agent is a peroxyacid according to the following formula:

$$R_3\text{—CO3H}$$

wherein $R_3$ is a substituted or unsubstituted, saturated or unsaturated, linear or branched hydrocarbon group having from 1 to 25 carbon atoms or a cyclic group having from 3 to 32 carbon atoms and optionally at least one heteroatom, or a cyclic alkyl group having from 4 to 32 carbon atoms and optionally at least one heteroatom, or a mixture thereof.

2. The article according to claim 1 wherein said oxidizing agent is selected from the group consisting of peroxygen bleaches, inorganic oxides, cerium compounds, lead compounds, manganese compounds, ozone, hydrazine and derivatives thereof.

3. The article according to claim 1 wherein $R_3$ in the peroxyacid formula is a substituted or unsubstituted, linear or branched, alkyl group or alkenyl group having from 1 to 25 carbon atoms, or an aryl alkyl group having from 4 to 32 total carbon atoms, or an aryl group having from 3 to 32 carbon atoms, or an heterocyclic group having from 3 to 32 carbon atoms and from 1 to 5 hetero atoms, or an heterocyclic alkyl group containing from 4 to 32 total carbon atoms and from 1 to 5 hetero atoms, wherein the hetero atoms are independently selected from the group consisting of oxygen, nitrogen and sulfur.

4. The article according to claim 1 wherein the oxidizing agent is a peroxyacid according to the formula:

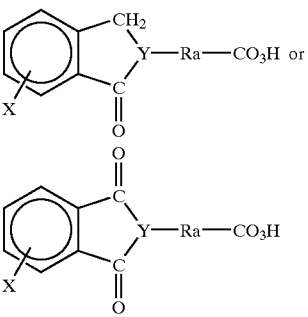

wherein Ra is a substituted or unsubstituted, saturated or unsaturated, linear or branched hydrocarbon group having from 1 to 14 carbon atoms, Y is an heteroatom and X are substituents in position ortho or meta independently selected from the group of hydrogen, hydroxy, halogen, carboxy, aliphatic saturated or unsaturated, linear or branched, hydrocarbon group having from 1 to 10 carbon atoms, or a mixture thereof.

5. The article according to claim 1 wherein said oxidizing agent is a diacyl peroxide according to the formula:

$$R_1\text{—C(O)—O—O—(O)C—}R_2$$

wherein $R_1$ and $R_2$ are the same or different and are selected from the group of substituted or unsubstituted, saturated or unsaturated, linear, branched or cyclic hydrocarbon groups having from 1 to 50 carbon atoms.

6. The article according to claim 5 wherein $R_1$ and $R_2$ in the diacyl peroxide formula are independently a mono or polycyclic aromatic ring, a homo or heteroaromatic ring, substituted or unsubstituted of from 2 to 50 total carbon atoms or a mixture thereof.

7. The article according to claim 1 wherein the oxidizing agent is a pthalimido peroxyalkanoic acid, a phtalamido peroxyalkanoic acid, dilauroyl peroxide, dibenzoyl peroxide and/or benzoyl lauroyl peroxide.

8. The article according to claim 1 which comprises from 1 $gm^{-2}$ to 250 $gm^{-2}$ of said oxidizing agent or a mixture thereof.

9. The article according to claim 1, wherein the hemolytic agent is a surfactant selected from the group consisting of nonionic surfactants, anionic surfactants, amphoteric surfactants, zwitterionic surfactants, biguanide and derivatives thereof, organic sulfur compounds, organic nitrogen compounds, phenyl and phenoxy compounds, phenolic compounds, aldehydes, parabens, organic acids, carboxylic acids, alcohols and mixtures thereof.

10. The article according to claim 1 wherein the hemolytic agent is a zwitterionic surfactant according to the following formula:

$$R_1\text{—}N^+(R_2)(R_3)R_4X^-$$

wherein $R_1$ is a hydrophobic group; $R_2$ is hydrogen, $C_1$–$C_6$ alkyl, hydroxy alkyl or other substituted C1–C6 alkyl group; $R_3$ is hydrogen, $C_1$–$C_6$ alkyl, hydroxy alkyl or other substituted $C_1$–$C_6$ alkyl group which can also be joined to $R_2$ to form ring structures with the N, or a $C_1$–$C_6$ carboxylic acid group or a $C_1$–$C_6$ sulfonate group; R4 is a moiety joining the cationic nitrogen atom to the hydrophilic group and is typically an alkylene, hydroxy alkylene, or polyalkoxy group containing from 1 to 10 carbon atoms or hydrogen; and X is the hydrophilic group selected from the group consisting of a carboxylate group, a sulphate group, a sulfonate group, an halogen and hydroxide.

11. The article according to claim 1 wherein the hemolytic agent is a quaternary ammonium surfactant.

12. The article according to claim 1 which comprises from 0.5 gm$^{-2}$ to 100 gm$^{-2}$ of an hemolytic agent or a mixture thereof.

13. The article according to claim 1, which further comprises an additional odour control agent selected from the group consisting of absorbing gelling materials, silicas, zeolites, carbons, starches, chelating agents, pH buffered materials, chitin, kieselguhr, clays, ion exchange resins, carbonates, bicarbonates, phosphates, sulphates, carboxylic acids and combination thereof.

14. The article according to claim 13 which comprises from 1 gm$^{-2}$ to 400 gm$^{-2}$ of said additional odour control agent or a mixture thereof.

15. The article according to claim 1 wherein said article is an absorbent disposable article.

16. The article according to claim 1 wherein said article is an absorbent disposable article comprising a liquid pervious topsheet, a backsheet and an absorbent core intermediate said backsheet and said topsheet.

* * * * *